United States Patent [19]

Nelson et al.

[11] 4,122,267

[45] Oct. 24, 1978

[54] CHLORINATED S-TRIAZINE TRIONE COMPOSITIONS AND PROCESS FOR THEIR PREPARATION

[75] Inventors: George D. Nelson, St. Louis; Kenneth J. Nissing, St. Charles; William F. Symes, St. Louis, all of Mo.

[73] Assignee: Monsanto Company, St. Louis, Mo.

[21] Appl. No.: 670,294

[22] Filed: Mar. 25, 1976

[51] Int. Cl.$^2$ .......................................... C07D 251/36
[52] U.S. Cl. ................................................. 544/190
[58] Field of Search ..................... 260/248 C; 544/190

[56] References Cited

U.S. PATENT DOCUMENTS

| | | | |
|---|---|---|---|
| 3,364,146 | 1/1968 | Casey et al. .......................... | 544/190 |
| 3,501,468 | 3/1970 | Moore et al. ......................... | 260/248 |
| 3,803,144 | 4/1974 | Berkowitz ............................. | 260/248 |
| 3,853,867 | 12/1974 | Berkowitz et al. .................. | 544/190 |
| 3,878,208 | 4/1975 | Carlson et al. ....................... | 260/248 |
| 3,894,018 | 7/1975 | Wojtowicz et al. ................. | 260/248 |
| 3,923,802 | 12/1975 | Hill ....................................... | 260/248 |

OTHER PUBLICATIONS

FMC Corporation, Product Promotion Bulletin 10B (1965) p. 1.

*Primary Examiner*—John M. Ford
*Attorney, Agent, or Firm*—N. E. Willis; E. P. Grattan; W. H. Duffey

[57] ABSTRACT

New chlorinated s-triazine trione compositions are prepared in essentially theoretical yields and with essentially no waste disposal requirements.

18 Claims, No Drawings

CHLORINATED S-TRIAZINE TRIONE COMPOSITIONS AND PROCESS FOR THEIR PREPARATION

BACKGROUND OF THE INVENTION

This invention relates to new chlorinated s-triazine trione compositions and processes for producing them. These compositions are produced in essentially theoretical yields and with essentially no waste disposal requirements.

Description of the Prior Art

Chlorinated s-triazine trione products are well known for use as bleaching and sanitizing compounds and compositions. Especially important chlorinated s-triazine trione products are sodium dichloro s-triazine trione (sometimes called sodium dichlorocyanurate), and trichloro s-triazine trione (sometimes called trichlorocyanuric acid). These compounds have found commercial importance in the area of water treatment where they have proved effective and convenient for combatting algae and pathogenic bacteria. Similarly useful chlorinated s-triazine trione products are dichloro s-triazine trione (sometimes called dichlorcyanuric acid), potassium dichloro s-triazine trione (sometimes called potassium dichlorocyanurate), the hydrated forms of both sodium and potassium dichloro s-triazine triones, mixtures thereof and complexes thereof, such as [(monotrichloro,) tetra-(monopotassium dichloro,)] penta-s-triazine trione and (monotrichloro,) (monopotassium dichloro), di-s-triazine trione, and mixtures thereof.

Because of the recognized usefulness of these products, methods for preparing them and improvements to methods for preparing them have received a great deal of attention.

One of the earliest methods for producing chlorinated s-triazine trione products was that disclosed in U.S. Pat. No. 2,607,738. This patent disclosed a method for producing trichlorocyanuric acid (trichloro s-triazine trione) which comprises dissolving cyanuric acid (s-triazine trione) in the theoretical quantity of a 5% solution of caustic potash or soda, and treating the resulting solution with chlorine until 3 atoms of the alkali have been substituted by chlorine. However, Chattaway and Wardmore, in the "Journal of the Chemical Society," volume 81, pages 200-202 (1902), point out that where relatively large quantities of reactants are used in the chlorination of cyanuric acid dissolved in the theoretical quantity of potash, low product yields and products low in available or active chlorine are obtained. Thus the foregoing batch process is not adaptable to large scale commercial production.

An improved process for producing chlorocyanuric acids (dichloro s-triazine trione and trichloro s-triazine trione) is disclosed by U.S. Pat. No. 2,964,525, which process resulted in increased yields. This process purportedly achieves yields as high as 85% by continuously reacting trisodium cyanurate (trisodium s-triazine trione) and chlorine in an aqueous solution under specified conditions of temperature and pH. It should be noted, however, that this reaction also produces, as a byproduct, sodium chloride. The disclosed process includes the further steps of separating the product from the bulk of the aqueous medium by filtration, decantation, centrifugation or the like; and washing the wet product with water to remove the sodium chloride contained therein prior to drying. These latter two steps result in an accumulation of an aqueous solution of by-products, which also may contain small amounts of the unreacted raw material as well as final product. The ultimate disposal of this waste stream represents a yield loss, a potential environmental problem, and at the very least, additional expenses related to proper waste treatment.

A process for preparing the sodium and potassium salts of dichlorocyanuric acid (sodium dichloro s-triazine trione and potassium dichloro s-triazine trione) is disclosed by U.S. Pat. No. 3,035,056. According to this process, chlorine is added to an aqueous solution of trisodium (or tripotassium) isocyanurate (trisodium s-triazine trione) at a specified temperature and pH range, to obtain a slurry of the reaction product (the sodium or potassium dichloro s-triazine trione) in an aqueous medium which also contains sodium or potassium chloride byproduct. The solid product is then separated from the aqueous slurry, which is subsequently discarded. This discarded liquid phase contains, in addition to sodium or potassium chloride byproduct, small amounts of the product itself. Thus, this process involves the disposal of a waste stream which represents a yield loss, a potential environmental problem, as well as an expense for proper treatment.

Therefore, the prior art methods for producing chlorinated s-triazine triones have a common deficiency. The deficiency is that these prior art methods produce, at some stage of the process, a waste stream which comprises water, an alkali metal salt byproduct, and certain amounts of the product itself dissolved in the water. Consequently, the prior art methods have (a) yield losses because they are literally throwing away product with their waste stream, (b) potential environmental problems due to the necessity of discarding of this waste stream, and (c) added expenses related to the disposal of this waste stream.

There are disclosed in the prior art techniques for recovering some of the useful product from this waste stream. Thus U.S. Pat. No. 3,758,463 discloses a method for recovering some of the cyanuric product from the aqueous waste stream before discarding the remainder. This method involves acidifying the mother liquor with a concentrated strong acid thereby precipitating the dissolved dichlorocyanurate values as dichlorocyanuric acid and separating the dichlorocyanuric acid precipitated from the mother liquor. Of course, the mother liquor still contains the sodium or potassium chloride, which must be disposed of. Therefore this art represents only a partial solution to the problem.

Another method of removing the dissolved chlorocyanurates from the waste stream is disclosed by U.S. Pat. No. 3,878,208. This method involves treating the waste stream with hydrogen peroxide whereby the chlorinated isocyanurate values are dechlorinated to cyanurate values, which precipitate out of the aqueous medium. However, the dissolved sodium or potassium chloride is not removed from the waste stream, and still must be disposed of. Thus, this technique also represents only a partial solution to the problem.

There are also disclosed in the prior art, techniques for improving product recovery by increasing the particle size of the final product. Thus, U.S. Pat. No. 3,120,522 discloses the use of a chlorinated hydrocarbon additive to increase particle size, U.S. Pat. No. 3,427,314 discloses a method of promoting agglomeration of the product particles and U.S. Pat. No. 3,453,274 discloses the use of an alkali metal hydrocarbon sulfonate to promote the size of final product particles. Although these techniques are of some help in improving the product recovery, they further complicate the process and are not complete solutions to the aforedescribed problems.

Therefore, a need exists for new chlorinated s-triazine trione compositions which can be produced by simple processes, in essentially theoretical yields and with essentially no waste disposal requirements.

Surprisingly and unexpectedly, we have discovered a new class of chlorinated s-triazine trione compositions which can be produced by simple processes, in essentially theoretical yields and with essentially no waste disposal requirements.

SUMMARY OF THE INVENTION

It is an object of this invention to provide new chlorinated s-triazine trione compositions. It is another object of this invention to provide processes for preparing these chlorinated s-triazine trione compositions which processes overcome the yield loss and waste disposal problems associated with the prior art. It is still another object of this invention to provide improved processes of preparing chlorinated s-triazine trione products which are more efficient and less complex than the prior art processes.

These and other objects, as will be apparent to those skilled in the art, are met by a composition consisting essentially of at least one chlorinated s-triazine trione and at least one alkali metal chloride. This composition may be produced by a process which comprises preparing a chlorinated s-triazine trione product by chlorinating s-triazine trione or an alkali metal salt thereof, in an aqueous slurry, and then converting the slurry to a solid composition by removing water from it.

This new chlorinated s-triazine trione composition is useful for essentially the same purposes and to the same effect as the chlorinated s-triazine trione products known to the prior art.

The process by which this new composition is produced essentially eliminates the waste disposal requirements of the prior art, because virtually everything which leaves the process becomes a part of the final product, and nothing is "wasted." The only thing which leaves this process other than the product itself is a stream of relatively clean water which, in certain instances, can be recycled back to the process.

In addition to eliminating the "waste stream" of the prior art, this process also eliminates many of the complexities of the prior art processes. For example, this process is not dependent upon the size of the chlorinated s-triazine trione particles for yield efficiency, as are some of the prior art processes. Therefore, the use of particle size promotion techniques or additives may be eliminated.

The essence of this process resides in the concept of directly converting the chlorinated s-triazine trione product slurry to a solid composition by removing waste from it. The removal of water from the slurry causes the byproduct alkali metal chloride and any dissolved chlorinated s-triazine trione to be concentrated into a solid composition together with the main body of chlorinated s-triazine trione product. The product yield is essentially theoretical, and nothing is discarded other than relatively pure water. Waste disposal needs are therefore virtually eliminated. The water may be removed by any of several well known techniques. These include, but are not limited to, tray drying, rotary drying, vacuum rotary drying, drum drying and spray drying; although spray drying is preferred. A discussion of these and other useful water removal techniques may be found in the Encyclopedia of Chemical Technology, Ed. by R. E. Kirk and D. F. Othmer, New York: The Interscience Encyclopedia, Inc. 1950, vol. 5, pages 232-265.

PREFERRED EMBODIMENTS

The preferred compositions of this invention consist essentially of at least one chlorinated s-triazine trione and byproduct alkali metal chloride formed in producing it. The alkali metal chloride is usually sodium chloride, potassium chloride or mixtures thereof.

In a more preferred embodiment, the amount of alkali metal chloride present in the composition is from 20% wt. to 75% wt. of the amount of chlorinated s-triazine trione present.

In another preferred embodiment, the compositions of this invention consist essentially of (a) at least one component selected from the group consisting of dichloro s-triazine trione, trichloro s-triazine trione, sodium dichloro s-triazine trione, potassium dichloro s-triazine trione, [(mono-trichloro,)-tetra(monopotassium dichloro,)] penta s-triazine trione, (mono-trichloro,) (monopotassium dichloro,) di-s-triazine trione, mixtures thereof and mixtures thereof with unchlorinated s-triazine; and (b) at least one component selected from the group consisting of sodium chloride, potassium chloride and mixtures thereof. Component (a) may be in anhydrous, monohydrate or dihydrate form.

In yet another preferred embodiment, component (b) is present in an amount of from about 20% wt. to about 75% wt. of the amount of component (a) present.

Exemplary of the compositions of this invention are the following mixtures: trichloro s-triazine trione and sodium chloride; trichloro s-triazine trione and potassium chloride; trichloro s-triazine trione, sodium chloride and potassium chloride; sodium dichloro s-triazine trione and sodium chloride; potassium dichloro s-triazine trione and potassium chloride; sodium dichloro s-triazine trione, potassium dichloro s-triazine trione, sodium chloride and potassium chloride; s-triazine trione, dichloro s-triazine trione and sodium chloride; s-triazine trione, dichloro s-triazine trione and potassium chloride; dichloro s-triazine trione and sodium chloride; dichloro s-triazine trione and potassium chloride; [(mono-trichloro,)-tetra(mono-potassium dichloro,)] penta s-triazine trione and potassium chloride; (mono-trichloro,) (monopotassium dichloro,) di-s-triazone trione and potassium chloride; and [(mono-trichloro,)-tetra-(monopotassium dichloro,)] penta s-triazine trione, (monotrichloro,) (monopotassium dichloro,) di-s-triazine trione and potassium chloride. As discussed above, the preferred amount of alkali metal chloride (sodium chloride, potassium chloride or mixtures thereof) in each of these compositions is from 20% wt. to 75% wt. of the amount of chlorinated s-triazine trione present.

A particularly preferred embodiment of this invention is a composition as described above wherein component (b) is sodium chloride and component (a) is sodium dichloro s-triazine trione. Most preferred is a composition consisting essentially of sodium dichloro s-triazine trione and sodium chloride wherein the sodium chloride is present in an amount of from about 40% wt. to about 60% wt. of the amount of sodium dichloro s-triazine trione present.

These compositions may be produced by a process which comprises preparing a chlorinated s-triazine trione in an aqueous slurry and converting the slurry to a solid composition by removing water from it. The chlorinated s-triazine triones which may be prepared include, but are not limited to, dichloro s-triazine trione, trichloro s-triazine trione, sodium dichloro s-triazine trione, potassium dichloro s-triazine trione, [(mono-trichloro), tetra-(monopotassium dichloro,)] penta-s-triazine trione, (mono-trichloro,) (monopotassium dichloro,)-di-s-triazine trione, mixtures thereof and mixtures thereof with unchlorinated s-triazine trione.

In a preferred embodiment, the chlorinated s-triazine trione is prepared by chlorinating s-triazine trione or an alkali metal salt thereof. The alkali metal salts which may be chlorinated include, but are not limited to, monosodium s-triazine trione, disodium s-triazine trione, trisodium s-triazine trione, monopotassium s-triazine trione, dipotassium s-triazine trione, sodium-potassium s-triazine trione complex salts and mixtures thereof. Specific examples of sodium-potassium s-triazine trione complex salts may be found described in U.S. Pat. No. 3,501,468 in which they are referred to as "sodium-potassium cyanurates."

It is generally known that some chlorinated s-triazine triones can exist in anhydrous, monohydrate, and dihydrate forms as well as in combinations thereof. Therefore, when removing water from the slurry to convert it to a solid in the practice of this invention, various degrees of water removal may be desired. In practicing the process of this invention, the water which is removed may be only the free water, or it may include some of the water of hydration, or it may include all of the water of hydration.

Another preferred embodiment of the process of this invention is a process for preparing chlorinated s-triazine trione compositions which comprises: (a) continuously feeding s-triazine trione in an aqueous slurry, chlorine, and an aqueous alkali metal hydroxide solution to a chlorinator, (b) maintaining the temperature and pH in the chlorinator and the relative feed rates of the s-triazine trione, alkali metal hydroxide and chlorine as required to obtain the desired degree of chlorination, (c) continously removing the slurry from the chlorinator and (d) removing the water from the slurry.

Preferred alkali metal hydroxides for use in step (a) are sodium hydroxide, potassium hydroxide and mixtures thereof.

The temperature and pH in step (b) are maintained at levels appropriate to the particular chlorinated s-triazine trione desired. Typical temperature, pH ranges, and feed ratios for the various chlorinated s-triazine triones are tabulated in Table 1.

Table 1

| Condition | Dichloro s-triazine trione | Trichloro s-triazine trione | Sodium dichloro s-triazine trione | Potassium dichloro s-triazine trione | [(mono-dichloro,) tetra-(monopotassium dichloro,)] penta s-triazine trione | (mono-dichloro,) (monopotassium dichloro,)di-s-triazine trione |
|---|---|---|---|---|---|---|
| pH range | 1.5 – 2.5 | 2.5 – 4.0 | 5 – 8.5 | 6 – 8 | 5 – 6 | 2.1 – 4.0 |
| Preferred pH range | 1.8 – 2.2 | 3.3 – 3.8 | 5.5 – 6.5 | 7 – 7.5 | 5.3 – 5.8 | 2.5 – 3.0 |
| Temperature Range (° C.) | 10 – 35 | 10 – 35 | 10 – 60 | 10 – 60 | 10 – 60 | 10 – 60 |
| Preferred Temperature Range (° C.) | 15 – 25 | 15 – 25 | 40 – 45 | 40 – 45 | 40 – 45 | 20 – 30 |
| Alkali metal hydroxide to s-triazine trione feed molar ratio | 2.0 – 2.20 | 3.0 – 3.3 | 2.0 – 2.20 | 2.0 – 2.20 | 3.0 – 3.2 | 3.0 – 3.30 |
| Preferred alkali metal to s-triazine trione feed molar ratio | 2.02 – 2.08 | 3.1 – 3.2 | 2.05 – 2.10 | 2.05 – 2.10 | 3.02 – 3.08 | 3.05 – 3.15 |

As previously noted, there are many techniques by which the water may be removed from the slurry to convert it to a solid. A preferred method of removing water from the slurry is that of spray drying.

Yet another preferred embodiment of this invention is a process for preparing chlorinated s-triazine trione compositions which process comprises all the steps given for the immediately preceding preferred embodiment except that subsequent to step (c) but prior to step (d) part of the liquid is removed from the slurry and recycled to the process. This can be accomplished, for example, by filtration or centrifugation. The liquid which is recycled to the process may be used as all or part of the aqueous media used in preparing the s-triazine trione slurry. For example, when practicing this preferred embodiment, sodium dichloro s-triazine trione may be prepared as follows: A feed slurry of s-triazine trione is formed by mixing s-triazine trione with an aqueous medium comprised of makeup water plus the mother liquor which is recycled from the product slurry filtration step of the process. Thus, when the process is initially "brought on stream" the aqueous medium will be primarily makeup water, while after the process is "on stream" the "mother liquor" which is recycled from the downstream product slurry filtration step may be used together with any needed makeup water to form the aqueous medium for the slurry. This feed slurry is then fed continuously to the chlorinator along with chlorine and an aqueous solution of sodium hydroxide. The feed rates of the s-triazine trione and sodium hydroxide are adjusted to maintain a sodium hydroxide to s-triazine trione feed weight ratio of about 3.1:1, and the chlorine feed rate is adjusted to maintain the pH in the chlorinator between 5.0 and 8.5, and preferably between 5.5 and 6.5. The temperature in the chlorinator is maintained at between 10° C. and 60° C., and preferably between 40° C. and 45° C., by direct or indirect cooling. Product slurry is continuously removed from the chlorinator and fed to a filter, where it is separated into a liquid filtrate and a filtercake. The liquid filtrate is recycled to the process to be used in making additional aqueous s-triazine trione feed slurry, and the filtercake proceeds on to the water removal step.

Although not necessary to the operability of this invention, and not a limitation thereof, it is preferred to cool the slurry leaving the chlorinator prior to filtering it. By precooling this slurry, filtration efficiency may be improved. In this regard, various cooling methods, such as flash cooling for example, may be employed. When cooling is employed, the slurry is cooled to a temperature of from about 20° C. to 45° C., and preferably to 25° C.

It may be desirable to vary the amount of mother liquor removed for recycling, for example, to achieve a desired balance between fresh makeup water and recycled mother liquor used in the feed preparation step. In a preferred embodiment of this invention, the amount of mother liquor removed from the slurry in the filtration step is varied by conducting the filtration in a vacuum filter and adjusting the absolute pressure in the filter to achieve the desired degree of filtration. In another preferred embodiment, the amount of mother liquor removed from the slurry is varied by filtering a part of the slurry while bypassing the filter with the remainder. The ratio of slurry fed to the filter to that bypassed is adjusted to obtain the desired amount of mother liquor.

It will be understood by those skilled in the art that various modifications to the operating conditions given in this preferred embodiment may be made, and various degrees of chlorination may be achieved, within the spirit of this invention. All variations of this process which include the removal of water from the slurry to convert it to a solid composition are within the scope of this invention.

Other modes of applying the principles of this invention will be apparent to those skilled in the art. Accordingly, while this invention has been described with reference to specific embodiments, it is understood that the invention is not limited to such specific embodiments and that it may be variously practiced within the scope of the following claims.

We claim:

1. A reaction product consisting essentially of at least one chlorinated s-triazine trione and byproduct alkali metal chloride formed in producing said trione, said byproduct alkali metal chloride being present in an amount of from about 20% weight to about 75% weight of the amount of chlorinated s-triazine trione present.

2. A reaction product as described in claim 1 wherein the alkali metal chloride is sodium chloride, potassium chloride or mixtures thereof.

3. A reaction product consisting essentially of
   (a) at least one component selected from the group consisting of dichloro s-triazine trione, trichloro s-triazine trione, sodium dichloro s-triazine trione, potassium dichloro s-trione, [(mono-trichloro,)tetra-(monopotassium dichloro,)] penta s-triazine trione, (mono-trichloro,) di-s-triazine trione, mixtures thereof and mixtures thereof with unchlorinated s-triazine trione; and
   (b) At least one component selected from the group consisting of sodium chloride, potassium chloride and mixtures thereof, wherein this component (b) is present in an amount of from about 20% weight to about 75% weight of the amount of component (a) present.

4. A reaction product as described in claim 3 wherein component (a) is in anhydrous, monohydrate or dihydrate form.

5. A reaction product as described in claim 3 wherein component (a) is sodium dichloro s-triazine trione and component (b) is sodium chloride.

6. A reaction product consisting essentially of sodium dichloro s-triazine trione and sodium chloride wherein the sodium chloride is present in an amount of from about 40% wt. to about 60% wt. of the amount of sodium dichloro s-triazine trione present.

7. A process for producing chlorinated s-triazine trione compositions containing from about 20% weight to about 75% weight, based upon the weight of said trione, of an alkali metal chloride which process comprises preparing said chlorinated s-triazine trione in an aqueous slurry and converting the slurry to a solid composition by removing water from the slurry.

8. A process as described in claim 7 wherein the water is removed by spray drying the slurry.

9. A process as described in claim 7 wherein only the free water is removed from the slurry.

10. A process as described in claim 7 wherein a part of the water of hydration of the chlorinated s-triazine trione is removed.

11. A process as described in claim 7 wherein all of the water of hydration of the chlorinated s-triazine trione is removed.

12. A process as described in claim 7 wherein the chlorinated s-triazine trione is selected from the group consisting of dichloro s-triazine trione, trichloro s-triazine trione, sodium dichloro s-triazine trione, potassium dichloro s-triazine trione, [(mono-trichloro,) tetra-(monopotassium dichloro,)] penta-s-triazine trione, (mono-trichloro,) (monopotassium dichloro,) di-s-triazine trione, mixtures thereof and mixtures thereof with unchlorinated s-triazine trione.

13. A process as described in claim 7 wherein the chlorinated s-triazine trione is prepared by chlorinating s-triazine trione or an alkali metal salt of an s-triazine trione.

14. A process as described in claim 13 wherein the alkali metal salt is selected from the group consisting of monosodium s-triazine trione, disodium s-triazine trione, trisodium s-triazine trione, monopotassium s-triazine trione, dipotassium s-triazine trione, tripotassium s-triazine trione, sodium-potassium s-triazine trione complex salts and mixtures thereof.

15. A process for preparing chlorinated s-triazine trione compositions containing from about 20% weight to about 75% weight, based upon the weight of trione present, of an alkali metal chloride, which process comprises:
   (a) continuously feeding s-triazine trione in an aqueous slurry, chlorine and an aqueous alkali metal hydroxide solution to a chlorinator,
   (b) maintaining the temperature and pH in the chlorinator and the relative feed rates of the s-triazine trione, alkali metal hydroxide and chlorine as required to obtain the desired degree of chlorination,
   (c) continuously removing the slurry from the chlorinator, and
   (d) removing water from the slurry.

16. A process as described in claim 15 wherein the alkali metal hydroxide is selected from the group consisting of sodium hydroxide, potassium hydroxide and mixtures thereof.

17. A process as described in claim 15 wherein subsequent to step (c) but prior to step (d) part of the liquid is removed from the slurry and recycled to the process.

18. A process as described in claim 15 wherein the water is removed by spray drying.

* * * * *